(12) United States Patent
Dorn et al.

(10) Patent No.: US 10,271,979 B2
(45) Date of Patent: Apr. 30, 2019

(54) STENT DELIVERY DEVICE WITH ROLLING STENT RETAINING SHEATH

(75) Inventors: Jurgen Dorn, Neulussheim (DE); Martina Hoffman, Stutensee (DE); Daniel Dietrich, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1372 days.

(21) Appl. No.: 12/650,863

(22) Filed: Dec. 31, 2009

(65) Prior Publication Data

US 2010/0168835 A1   Jul. 1, 2010

Related U.S. Application Data

(60) Provisional application No. 61/141,859, filed on Dec. 31, 2008.

(30) Foreign Application Priority Data

Dec. 31, 2008  (GB) .................................. 0823716.6

(51) Int. Cl.
*A61F 2/95* (2013.01)
*A61F 2/966* (2013.01)

(52) U.S. Cl.
CPC .............. *A61F 2/966* (2013.01); *A61F 2/95* (2013.01); *A61F 2002/9522* (2013.01)

(58) Field of Classification Search
CPC .. A61F 2/95; A61F 2/962; A61F 2/966; A61F 2002/9522
USPC ............................................... 623/1.11, 1.12
See application file for complete search history.

(56) References Cited

U.S. PATENT DOCUMENTS

| 3,953,566 | A | 4/1976 | Gore |
| 3,962,153 | A | 6/1976 | Gore |
| 4,187,390 | A | 2/1980 | Gore |
| 4,732,152 | A | 3/1988 | Wallsten et al. |
| 5,087,394 | A | 2/1992 | Keith |

(Continued)

FOREIGN PATENT DOCUMENTS

| DE | 10339628 A1 | 3/2005 |
| EP | 0732087 A1 | 9/1996 |

(Continued)

OTHER PUBLICATIONS

PCT/EP2009/064057 filed Oct. 26, 2009 International Preliminary Report on Patentability dated Jun. 6, 2011.

(Continued)

*Primary Examiner* — Katherine M Rodjom
(74) *Attorney, Agent, or Firm* — Rutan & Tucker, LLP

(57) ABSTRACT

A delivery device for delivering a stent device that is expandable from a radially reduced, delivery configuration to a radially expanded, deployed configuration. A retaining sheath is disposed over the stent device for maintaining the stent device in the delivery configuration. A pull line to be pulled upon is provided to retract the retaining sheath in a rolling manner such that the retaining sheath is folded back on itself to provide a radially inner sheath of the retaining sheath, a radially outer sheath of the retaining sheath and a fold portion therebetween. The retaining sheath may be made of a cold drawn plastic at least along the path of travel of the fold portion in retracting the retaining sheath from over the stent device.

10 Claims, 3 Drawing Sheets

(56) References Cited

U.S. PATENT DOCUMENTS

| | | |
|---|---|---|
| 5,217,482 A | 6/1993 | Keith |
| 5,324,261 A | 6/1994 | Amundson et al. |
| 5,453,090 A | 9/1995 | Martinez et al. |
| 5,573,520 A | 11/1996 | Schwartz et al. |
| 5,626,605 A | 5/1997 | Irie et al. |
| 5,662,703 A | 9/1997 | Yurek et al. |
| 5,690,644 A | 11/1997 | Yurek et al. |
| 5,709,703 A | 1/1998 | Lukic et al. |
| 5,718,861 A | 2/1998 | Andrews et al. |
| 5,755,769 A | 5/1998 | Richard et al. |
| 5,765,682 A | 6/1998 | Bley et al. |
| 5,823,995 A | 10/1998 | Fitzmaurice et al. |
| 5,824,041 A | 10/1998 | Lenker et al. |
| 5,833,694 A | 11/1998 | Poncet |
| 5,843,027 A | 12/1998 | Stone et al. |
| 5,968,069 A | 10/1999 | Dusbabek et al. |
| 5,992,000 A | 11/1999 | Humphrey et al. |
| 6,027,510 A | 2/2000 | Alt |
| 6,063,092 A | 5/2000 | Shin |
| 6,126,685 A | 10/2000 | Lenker et al. |
| 6,149,681 A | 11/2000 | Houser et al. |
| 6,168,748 B1 | 1/2001 | Wang et al. |
| 6,254,628 B1* | 7/2001 | Wallace et al. .............. 623/1.12 |
| 6,425,898 B1 | 7/2002 | Wilson et al. |
| 6,447,540 B1 | 9/2002 | Fontaine et al. |
| 6,544,278 B1* | 4/2003 | Vrba ...................... A61F 2/01 |
| | | 606/192 |
| 6,613,067 B1 | 9/2003 | Johnson |
| 6,613,075 B1 | 9/2003 | Healy et al. |
| 6,645,238 B2 | 11/2003 | Smith |
| 6,702,843 B1 | 3/2004 | Brown et al. |
| 6,805,703 B2 | 10/2004 | McMorrow |
| 6,833,002 B2 | 12/2004 | Stack et al. |
| 6,841,029 B2 | 1/2005 | Lim |
| 6,946,092 B1 | 9/2005 | Bertolino et al. |
| 7,128,956 B2 | 10/2006 | Wang et al. |
| 7,815,669 B2 | 10/2010 | Matsuoka et al. |
| 8,568,467 B2 | 10/2013 | Dorn et al. |
| 9,687,370 B2 | 6/2017 | Dorn |
| 2001/0011180 A1 | 8/2001 | Fitzmaurice et al. |
| 2001/0027323 A1 | 10/2001 | Sullivan et al. |
| 2002/0016597 A1 | 2/2002 | Dwyer et al. |
| 2003/0109886 A1 | 6/2003 | Keegan et al. |
| 2003/0114912 A1 | 6/2003 | Sequin et al. |
| 2003/0125709 A1 | 7/2003 | Eidenschink |
| 2003/0139796 A1* | 7/2003 | Sequin .................. A61F 2/915 |
| | | 623/1.12 |
| 2003/0139801 A1 | 7/2003 | Sirhan et al. |
| 2003/0163193 A1 | 8/2003 | Widenhouse |
| 2003/0204235 A1 | 10/2003 | Edens et al. |
| 2004/0143272 A1* | 7/2004 | Cully ...................... A61F 2/95 |
| | | 606/108 |
| 2004/0143315 A1 | 7/2004 | Bruun et al. |
| 2004/0148007 A1 | 7/2004 | Jackson et al. |
| 2004/0199239 A1 | 10/2004 | Austin et al. |
| 2004/0267346 A1 | 12/2004 | Shelso |
| 2005/0004555 A1 | 1/2005 | Pursley |
| 2005/0049667 A1 | 3/2005 | Arbefeuille et al. |
| 2005/0113902 A1 | 5/2005 | Geiser et al. |
| 2005/0240254 A1* | 10/2005 | Austin ..................... 623/1.11 |
| 2006/0015171 A1 | 1/2006 | Armstrong |
| 2006/0025844 A1* | 2/2006 | Majercak ................ A61F 2/95 |
| | | 623/1.11 |
| 2006/0030923 A1 | 2/2006 | Gunderson |
| 2006/0089627 A1 | 4/2006 | Burnett et al. |
| 2006/0200221 A1 | 9/2006 | Malewicz |
| 2006/0212105 A1 | 9/2006 | Dorn et al. |
| 2006/0247661 A1 | 11/2006 | Richards et al. |
| 2006/0259124 A1 | 11/2006 | Matsuoka et al. |
| 2007/0050017 A1 | 3/2007 | Sims et al. |
| 2007/0074805 A1 | 4/2007 | Leeflang et al. |
| 2007/0088421 A1* | 4/2007 | Loewen .................. A61F 2/95 |
| | | 623/1.11 |
| 2008/0118546 A1 | 5/2008 | Thatcher et al. |
| 2008/0243224 A1 | 10/2008 | Wallace et al. |
| 2009/0125093 A1* | 5/2009 | Hansen .................. 623/1.11 |
| 2009/0254169 A1 | 10/2009 | Spenser et al. |
| 2009/0312828 A1 | 12/2009 | Vrba |
| 2010/0049297 A1 | 2/2010 | Dorn |
| 2010/0249907 A1 | 9/2010 | Dorn et al. |
| 2011/0060397 A1 | 3/2011 | Dorn |
| 2011/0137396 A1 | 6/2011 | Dorn et al. |
| 2011/0137400 A1 | 6/2011 | Dorn et al. |
| 2011/0137401 A1 | 6/2011 | Dorn et al. |
| 2011/0137402 A1 | 6/2011 | Dorn et al. |
| 2012/0059448 A1 | 3/2012 | Parker et al. |
| 2012/0143303 A1 | 6/2012 | Dorn et al. |
| 2018/0333284 A1 | 11/2018 | Dorn et al. |

FOREIGN PATENT DOCUMENTS

| | | |
|---|---|---|
| EP | 0941713 A1 | 9/1999 |
| EP | 1062966 A1 | 12/2000 |
| EP | 0732087 B1 | 6/2003 |
| EP | 1679095 A1 | 7/2006 |
| FR | 2688688 A1 | 9/1993 |
| JP | S59-51863 A | 3/1984 |
| JP | H09-512194 A | 12/1997 |
| JP | 2000-116788 A | 4/2000 |
| JP | 2001-9037 | 1/2001 |
| JP | 2001-299926 A | 10/2001 |
| JP | 2006-515786 A | 6/2006 |
| WO | 8603398 A1 | 6/1986 |
| WO | 1993017636 A1 | 9/1993 |
| WO | 9415549 A1 | 7/1994 |
| WO | 1995030385 A1 | 11/1995 |
| WO | 9632078 A1 | 10/1996 |
| WO | 1998020812 A1 | 5/1998 |
| WO | 2000018329 A1 | 4/2000 |
| WO | 2001008599 A1 | 2/2001 |
| WO | 02/38084 A2 | 5/2002 |
| WO | 03002034 A2 | 1/2003 |
| WO | 2003002019 A2 | 1/2003 |
| WO | 2004062458 A2 | 7/2004 |
| WO | 2004066809 A2 | 8/2004 |
| WO | 2004096091 A1 | 11/2004 |
| WO | 2005072650 A1 | 8/2005 |
| WO | 2006019626 A2 | 2/2006 |
| WO | 2006020028 A1 | 2/2006 |
| WO | 2006071245 A1 | 7/2006 |
| WO | 2006086709 A1 | 8/2006 |
| WO | 2006096229 A1 | 9/2006 |
| WO | 2006130326 A2 | 12/2006 |
| WO | 2007103666 A2 | 9/2007 |
| WO | 2009050265 A1 | 4/2009 |
| WO | 2009135934 A1 | 11/2009 |
| WO | 2010076052 A1 | 7/2010 |
| WO | 2010076057 A1 | 7/2010 |
| WO | 2010115925 A1 | 10/2010 |
| WO | 2011067277 A1 | 6/2011 |
| WO | 2011067280 A1 | 6/2011 |
| WO | 2012072729 A1 | 6/2012 |

OTHER PUBLICATIONS

EP 0815339.7 filed Aug. 21, 2008 Search Report dated Dec. 22, 2008.
EP 12164925.5 filed Jul. 6, 2011 Extended European Search Report dated Jul. 26, 2012.
PCT/EP2009/055592 filed May 8, 2009 International Preliminary Report on Patentability dated Nov. 9, 2010.
PCT/EP2009/055592 filed May 8, 2009 Search Report dated Aug. 3, 2009.
PCT/EP2009/055592 filed May 8, 2009 Written Opinion dated Aug. 3, 2009.
PCT/EP2009/060827 filed Aug. 21, 2009 Preliminary Report on Patentability dated Oct. 19, 2010.
PCT/EP2009/060827 filed Aug. 21, 2009 Search Report dated Nov. 16, 2009.
PCT/EP2009/060827 filed Aug. 21, 2009 Written Opinion dated Nov. 16, 2009.

(56) References Cited

OTHER PUBLICATIONS

PCT/EP2009/064057 filed Oct. 26, 2009 International Search Report dated May 17, 2010.
PCT/EP2009/064057 filed Oct. 26, 2009 Written Opinion dated May 17, 2010.
PCT/EP2010/068620 filed Dec. 1, 2010 International Preliminary Report on Patentability dated Aug. 5, 2011.
PCT/EP2010/068620 filed Dec. 1, 2010 International Search Report dated Apr. 21, 2011.
PCT/EP2010/068620 filed Dec. 1, 2010 Written Opinion dated Apr. 21, 2011.
PCT/EP2010/068627 filed Dec. 1, 2010 International Preliminary Report on Patentability dated Jul. 20, 2011.
PCT/EP2010/068627 filed Dec. 1, 2010 International Search Report dated Apr. 21, 2011.
PCT/EP2010/068627 filed Dec. 1, 2010 Written Opinion dated Apr. 21, 2011.
PCT/EP2011/071489 filed Dec. 1, 2011 International Search Report dated Mar. 6, 2012.
U.S. Appl. No. 12/545,409, filed Aug. 21, 2009 Non-Final Office Action dated Apr. 13, 2012.
U.S. Appl. No. 12/991,112, filed Nov. 4, 2010 Non-Final Office Action dated Apr. 3, 2012.
Nicholson, The Chemistry of Polymers, chapter 7, pp. 105-107 (printed Oct. 28, 2015).
Casas, et al. Cold drawing of polymers: Plasticity and aging, Journal of Non-Crystalline Solids 352, pp. 5076-5080 (2006).
Lazurkin, Cold-drawing of glass-like and crystalline polymers, Journal of Polymer Science (Jul. 1958).
Condensation Polymers, http://www.4college.co.uk/a/dp/condensation.php, (printed Oct. 28, 2015).
Landell et al., Mechanical Properties of Polymers and Composites, Second Edition, p. 299 (printed Oct. 28, 2015).
Coleman, On the cold Drawing of Polymers, Comp & Maths with Appls vol. 11, Nos. 1-3, pp. 35-65 (Pergamon Press Ltd, 1985).
Roberston, On the cold-drawing of plastics, Journal of Applied Polymer Science, vol. 7, issue 2, pp. 443-450 (Mar./Apr. 1963).
Reusch, Polymers, https://www2.chemistry.msu.edu/faculty/reusch/VirtTxtJml/polymers.htm (dated May 5, 2013, printed Oct. 28, 2015).
Lai, Study on Modification of Polymer Properties by the Cold Drawing Process, Soft, 2015, 4, 1-7, (Scientific Research Publishing Inc., Jan. 13, 2015).
Vincent, The necking and cold-drawing of rigid plastics, Polymer, vol. 1, pp. 7-19, Abstract only, (Elsevier Ltd, 1960).
James, Theory for the Cold-Drawing of Polymers, http://static-content.springer.com/lookinside/chp:10.1007/BFb0072155/...(printed Oct. 28, 2015).
JP 2011-523429 Office Action dated Jan. 6, 2014.
JP 2011-523429 Office Action dated Jul. 17, 2013.
PCT/EP2008/064036 filed Oct. 17, 2008 International Preliminary Examination Report dated Apr. 20, 2010.
PCT/EP2008/064036 filed Oct. 17, 2008 Search Report dated Jan. 22, 2009.
PCT/EP2008/064036 filed Oct. 17, 2008 Written Opinion dated Jan. 22, 2009.
U.S. Appl. No. 12/545,409, filed Aug. 21, 2009 Final Office Action dated Nov. 20, 2013.
U.S. Appl. No. 12/545,409, filed Aug. 21, 2009 Non-Final Office Action dated Apr. 29, 2013.
U.S. Appl. No. 12/738,568, filed Apr. 16, 2010 Advisory Action dated Jun. 10, 2011.
U.S. Appl. No. 12/738,568, filed Apr. 16, 2010 Final Office Action dated Mar. 29, 2013.
U.S. Appl. No. 12/738,568, filed Apr. 16, 2010 Non-Final Office Action dated Nov. 2, 2012.
U.S. Appl. No. 12/958,089, filed Dec. 1, 2010 Advisory Action dated Oct. 28, 2011.
U.S. Appl. No. 12/958,089, filed Dec. 1, 2010 Final Office Action dated Aug. 15, 2011.
U.S. Appl. No. 12/958,089, filed Dec. 1, 2010 Non-Final Office Action dated Jun. 20, 2014.
U.S. Appl. No. 12/958,089, filed Dec. 1, 2010 Non-Final Office Action dated Mar. 14, 2013.
U.S. Appl. No. 12/958,123, filed Dec. 1, 2010 Advisory Action dated Oct. 17, 2011.
U.S. Appl. No. 12/958,123, filed Dec. 1, 2010 Final Office Action dated Nov. 19, 2014.
U.S. Appl. No. 12/958,123, filed Dec. 1, 2010 Non-Final Office Action dated Jun. 11, 2014.
U.S. Appl. No. 12/958,123, filed Dec. 1, 2010 Non-Final Office Action dated Mar. 25, 2013.
U.S. Appl. No. 12/958,184, filed Dec. 1, 2010 Advisory Action dated Nov. 5, 2013.
U.S. Appl. No. 12/958,184, filed Dec. 1, 2010 Final Office Action dated Aug. 14, 2013.
U.S. Appl. No. 12/958,184, filed Dec. 1, 2010 Non-Final Office Action dated Mar. 14, 2013.
U.S. Appl. No. 12/958,220, filed Dec. 1, 2010 Advisory Action dated Nov. 5, 2013.
U.S. Appl. No. 12/958,220, filed Dec. 1, 2010 Final Office Action dated Aug. 13, 2013.
U.S. Appl. No. 12/958,220, filed Dec. 1, 2010 Non-Final Office Action dated Mar. 15, 2013.
U.S. Appl. No. 12/991,112, filed Nov. 4, 2010 Advisory Action dated Dec. 23, 2014.
U.S. Appl. No. 12/991,112, filed Nov. 4, 2010 Final Office Action dated May 9, 2013.
U.S. Appl. No. 12/991,112, filed Nov. 4, 2010 Final Office Action dated Sep. 11, 2014.
U.S. Appl. No. 12/991,112, filed Nov. 4, 2010 Non-Final Office Action dated Mar. 21, 2014.
U.S. Appl. No. 13/309,420, filed Dec. 1, 2011 Advisory Action dated Feb. 13, 2014.
U.S. Appl. No. 13/309,420, filed Dec. 1, 2011 Final Office Action dated Nov. 8, 2013.
U.S. Appl. No. 13/309,420, filed Dec. 1, 2011 Non-Final Office Action dated Apr. 15, 2013.
U.S. Appl. No. 12/958,220, filed Dec. 1, 2010 Notice of Allowance dated Jan. 2, 2019.
U.S. Appl. No. 15/436,597, filed Feb. 17, 2017 Non-Final Office Action dated Dec. 31, 2018.

* cited by examiner

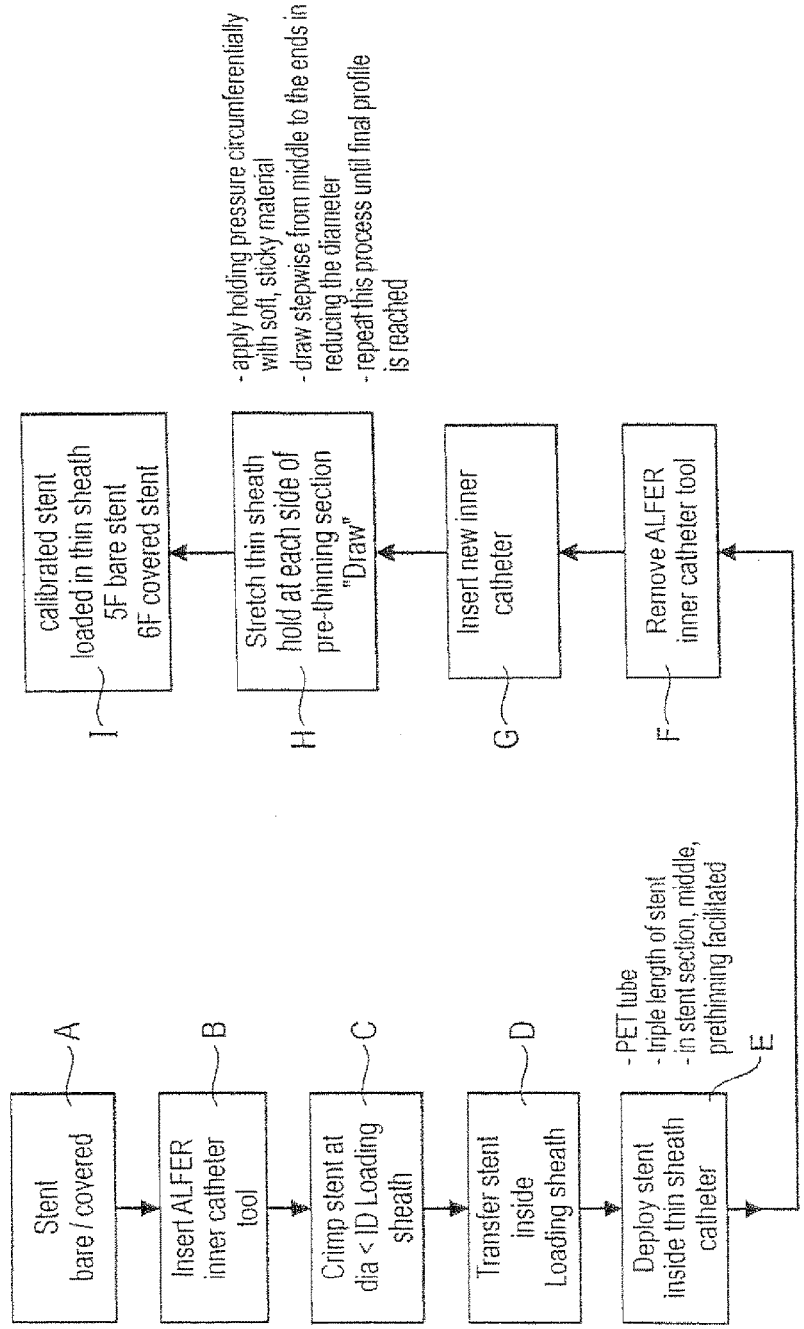

STENT DELIVERY DEVICE WITH ROLLING STENT RETAINING SHEATH

PRIORITY

This application is a continuation application of International Application No. PCT/EP2009/064057, filed Oct. 26, 2009, and claims the benefit of priority to U.S. Provisional Application No. 61/141,859, filed Dec. 31, 2008, and to U.K. Application No. 0823716.6, filed Dec. 31, 2008, each of which application is incorporated by reference in its entirety into this application.

FIELD

The present invention relates to a device for delivering a stent device to a treatment site. The device includes a retaining sheath for maintaining the stent device in a radially reduced, delivery configuration. At the treatment site, the retaining sheath is retracted so that the stent can radially expand to a deployed configuration for holding open and supporting a bodily lumen. The present invention is more particularly concerned with a delivery device having a rolling retaining sheath that rolls back over the stent device in order to retract the retaining sheath and thus allow expansion of the stent device. A pull member is provided that is connected to the retaining sheath and that is moveable to retract the retaining sheath.

BACKGROUND

Stent devices are known to the skilled person. They are used to hold open various bodily lumens. Of particular interest to the present invention are stent devices for supporting a wall of a vein or artery. Stent devices can self-expand into a deployed configuration or can be forcibly expanded such as by inflating a balloon within a lumen of the stent device. Self-expanding stent devices can be made of shape memory material. One example of a suitable shape memory material is the shape memory nickel titanium alloy known as Nitinol.

Stent devices may be provided in a number of forms. One example of which has a framework of axially spaced rings of zigzagging struts. The rings are centred on a common axis. The rings are connected to an adjacent ring by several connector struts. When a stent graft is being made, the framework is covered by a liquid impermeable material. The cover may be expanded polytetrafluoroethylene (ePTFE). When a bare stent is being made, the framework is left uncovered.

Generally, a stent device is crimped onto an inner tubular member in a delivery configuration at a distal end of a delivery device. A retaining sheath is disposed coaxially over the stent device to maintain the stent device in the radially reduced delivery configuration. A pull member of some kind is provided for retracting the retaining sheath, thereby leaving the stent device free to expand to the deployed configuration. The pull member is associated with an actuation mechanism provided at a proximal end of the delivery device, perhaps at a handle of the delivery device if one is included, for operation by a medical professional for affecting retraction of the retaining sheath. There is a class of retaining sheaths that are retracted in a "rolling" manner as will be described below. It is with this kind of retaining sheath retraction mechanism that the present is concerned.

Delivery devices having rolling retaining sheaths are known in the prior art. Example prior disclosures can be found in the following patent publications: WO 2007/103666, WO 02/38084, WO 2004/066809, WO 03/002034, WO 86/03398, WO 94/15549, WO 96/32078, WO 2006/020028 and WO 2006/096229, each of which is incorporated by reference in its entirety into this application.

In these prior art disclosures, the retaining sheath is folded back onto itself so as to provide an inner sheath and an outer sheath disposed over the stent device and extending axially along the stent device. A fold portion is formed between the inner sheath and the outer sheath. The inner sheath is attached to the inner member at a position proximal of the stent device. The outer sheath is attached to a pull member. As the pull member is pulled upon and moved axially, the outer sheath moves with it, causing the fold portion to move or "roll" as well. As the fold portion moves with respect to the stent device, the stent device is progressively uncovered from the retaining sheath and is thus free to expand to the deployed configuration.

The rolling mechanism for retracting a retaining sheath is advantageous in a number of ways. A reduced pulling force retraction is provided as compared to withdrawing the retaining sheath by sliding the retaining sheath over the stent device. This can be imagined by comparing the ease with which one rolls a sock off of a foot as compared to trying to slide it off of the foot from the toe end. Thus, problems associated with excessive axial forces on the stent device during sheath retraction are less relevant. Furthermore, it is a retraction method that removes the retaining sheath from the body, as opposed to mechanisms that cut open the sheath and leave it caught between the expanded stent device and an inner sheath of the bodily lumen.

One object of the present invention is to provide a delivery device with a rolling retaining sheath that rolls in a reliable, predictable and low pulling force manner. A yet further objective of the present invention is to provide a delivery device with such a rolling retaining sheath that has a reduced profile in the region where the stent device and the retaining sheath is located.

SUMMARY

In a first aspect, the present invention provides a delivery device, including a stent device that is expandable from a radially reduced, delivery configuration to a radially expanded, deployed configuration, a retaining sheath disposed over the stent device for maintaining the stent device in the delivery configuration, a pull member to be pulled upon to retract the retaining sheath in a rolling manner such that the retaining sheath is folded back on itself to provide a radially inner sheath of the retaining sheath, a radially outer sheath of the retaining sheath and a fold portion therebetween, wherein the pull member is moveable by pulling thereon to move the outer sheath over the inner sheath and thus to move the fold portion axially relative to the stent device to retract the retaining sheath from over the stent device to release the stent device for expansion to the deployed configuration, wherein the retaining sheath is made of a cold drawn plastic at least along the path of travel of the fold portion in retracting the retaining sheath from over the stent device.

It has been found by the present inventors that making the retaining sheath of a cold drawn plastic eases the passage of the fold portion and thus the retraction of the retaining sheath. Furthermore, cold drawn plastics are thin, but sufficiently strong, which enables a reduced profile to the region of the delivery device where the stent device and the retaining sheath are located.

A cold drawn plastic sheath is a plastic tube that has been significantly axially elongated (for example elongated by 100-500%), yet maintained at a temperature below the plastic's glass transition temperature (or its lowest glass transition temperature if it has more than one) during the elongation. The wall of the plastic sheath is reduced in thickness, while the molecules of the plastic are substantially uniaxially aligned. A cold drawn material exhibits increased tensile strength and stiffness. It is speculated that one of the reasons for the easy rolling of a retaining sheath so made is related to this molecular alignment. The increased tensile strength allows thinner layers to carry out satisfactory stent device retention.

In a second aspect, the present invention provides a delivery device, including a stent device that is expandable from a radially reduced, delivery configuration to a radially expanded, deployed configuration, a retaining sheath disposed over the stent device for maintaining the stent device in the delivery configuration, a pull member to be pulled upon to retract the retaining sheath in a rolling manner such that the retaining sheath is folded back on itself to provide a radially inner sheath of the retaining sheath, a radially outer sheath of the retaining sheath and a fold portion therebetween, wherein the pull member is moveable by pulling thereon to move the outer sheath over the inner sheath and thus to move the fold portion axially relative to the stent device to retract the retaining sheath from over the stent device to release the stent device for expansion to the deployed configuration, wherein the pull member is a pull line, wherein the pull line extends axially along the stent device and joins the retaining sheath at or beyond an axial end of the stent device in a pre-retracted configuration of the retaining sheath.

According to the second aspect of the invention, a pull line is used to retract the retaining sheath. A pull line is a line extending axially, which will have a significantly smaller circumferential extent about the stent device as compared to the full tube of the retaining sheath. Often in the prior art, the inner and outer sheaths both extend over the full length of the stent device. The delivery device of the second aspect of the present invention, instead, allows a single walled retaining sheath, which extends over the stent device. A pull line extends from a first end of the stent device to an opposite second end of the stent device in order to join with the retaining sheath at or beyond the opposite end to allow retraction of the retaining sheath progressively from the second end. Accordingly, a reduced profile of the delivery device, in a region where the stent device and the retaining sheath are located, is possible.

Although the pull line is described as joining the retaining sheath, this term is used to identify the junction between the two members. The pull line may, in one preferred form, be formed integrally with the retaining sheath or it may, in another preferred form, be made of a different material to the retaining sheath and attached to the retaining sheath. In the latter form, the pull line may be radially thinner than a wall of the retaining sheath. A plastic thread for the pull line is envisaged. Alternatively, the pull line can be made of metal wire. A plastic thread may be preferable in terms of attachment to the retaining sheath. In the embodiment wherein the pull line and the retaining sheath are integral, a plurality of axial slits could be made in an end of the retaining sheath and the resulting strips of retaining sheath material could be spun into a thread, which is folded back to extend back along the stent device to provide the pull line. Alternatively, an end of the retaining sheath could cut away to leave a strip of material, which is folded back to extend back over the stent device to provide the pull line.

The second aspect and the first aspect are preferably combined. So, the retaining sheath of the second aspect of the present invention is preferably made of a cold drawn plastic in the manner defined above. Such a material is sufficiently strong to allow single-walled retention of the stent device, yet thin also.

It may be that the retaining sheath only folds back once the pull member is moved, thereby causing an end of the retaining sheath to fold back. It is preferred, however, that pre-retraction, the retaining sheath is folded back upon itself to define an outer sheath, an inner sheath and a fold portion therebetween. This will provide an easier pulling force for initiating retraction of the retaining sheath as compared to if the fold portion is to be formed upon initial movement of the pull member.

Preferably, the stent device is mounted on a supporting inner member. The inner sheath of the retaining sheath is attached to the inner member at a position proximal of the stent device. Also preferably, the pull line extends axially from a proximal end to a distal end of the stent device and joins the retaining sheath substantially at, or distal of, the distal end of the stent device. Preferably, the pull line joins with the outer sheath of the retaining sheath.

Preferably, the delivery device has a distal tip member. The distal tip member includes a radial recess. Preferably, the fold portion of the retaining sheath is positioned axially within the recess. Preferably, in the embodiment with a pull line, the outer sheath of the retaining sheath ends axially within the recess.

Preferably, the pull member comprises a stiffer, radially thicker portion and a more flexible, radially thinner portion and a coupler therebetween for coupling the portions. The stiffer portion provides a pull end of the pull member and the more flexible portion extends axially along the stent device. This allows a sufficiently strong and operable pull end as well as a reduced profile end region of the delivery device where the stent device and retaining sheath are located. Preferably, the coupler is a coupling ring mounted about the inner member and axially moveable relative thereto.

The delivery device may comprise an introducer member from which the retainer sheath distally extends. The pull member extends through the introducer member so that the retainer sheath is pulled axially into the introducer member during retraction. The coupler is positioned axially within the introducer member.

Preferably, the cold drawn plastic is a cold drawn polyester. More preferably, the cold drawn plastic is cold drawn polyethylene terephthalate (PET).

The stent device is preferably a self expanding stent device. The stent device is preferably made of a shape memory material, such as the nickel titanium shape memory alloy Nitinol. The stent device may comprise a number of spaced rings of zigzagging connector struts that are centred on a common axis. The spaced rings are each connected to another ring by several connector struts.

Presently preferred embodiments of the present invention are described in detail in the following with reference to the figures.

BRIEF DESCRIPTION OF THE DRAWINGS

FIG. 6 discloses a flow diagram of method steps for installing a stent or stent graft within a sheath.

DETAILED DESCRIPTION

Figure 1:
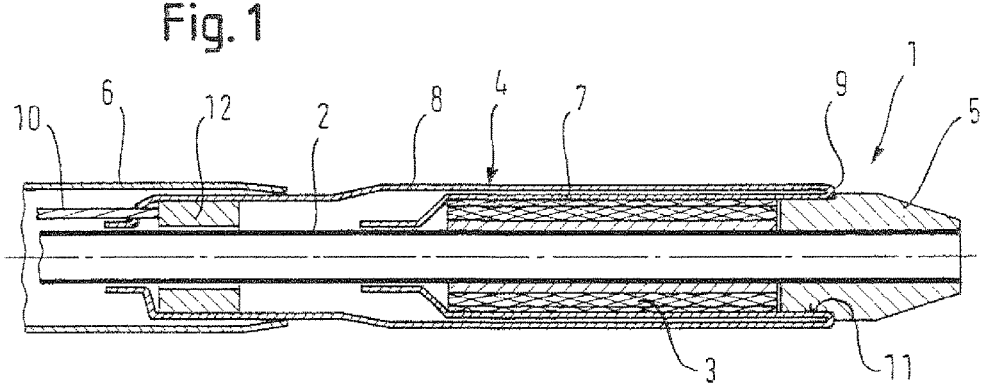
FIG. 1 discloses a first embodiment of a delivery device of the first aspect of the present invention having a retaining sheath that is retractable by rolling, wherein the retaining sheath is double-walled along a full length of a stent device and an outer wall of the retaining sheath extends proximally of the stent device to be coupled to a pull member.

A delivery device 1 according to a preferred embodiment of a first aspect of the present invention is shown in FIG. 1.

The delivery device 1 comprises a tubular inner member 2 having a stent device 3 crimped thereon in a radially reduced, delivery configuration at a distal end region of the inner member 2. The inner member 2 serves to radially support the stent device 3 in the delivery configuration. A tubular retaining sheath 4 is disposed over the stent device 3 for maintaining the stent device 3 in the delivery configuration. The retaining sheath 4 is to be retracted in order to release the stent device 3 for radial expansion to a deployed configuration. A distal tip member 5, providing a distal tip of the delivery device 1, is also included, which is attached to a distal end of the inner member 2 and which abuts a distal end of the stent device 3. The delivery device 1 further includes a tubular introducer member 6 through which the inner member 2 extends. The distal region of the inner member 2, where the stent device 3 lies, extends distally from a distal end of the inner member 2.

The retaining sheath 4 is retracted by a rolling mechanism, as is discussed in the following. An inner sheath 7 of the retaining sheath 4 is attached to the inner member 2 at a position proximal of the stent device 3. The inner sheath 7 extends radially over and axially along the stent device 2 to a position distal of the stent device 2 whereat the inner sheath 7 is folded back to provide an outer sheath 8 and a fold portion 9 between the inner and outer sheaths 7, 8. The outer sheath 8 extends radially over the inner sheath 7 and to a position proximal of the stent device 3. At its proximal end, and axially within the introducer member 6, the outer sheath 8 is coupled to a pull member 10 in the form of a metallic pull wire. A coupling ring 12 is provided for fixedly coupling the outer sheath 8 to the pull member 10. Both the pull member 10 and the outer sheath 8 are fixed to the coupling ring 12. The coupling ring 12 is axially slideable along the inner member 2. The pull member 10 extends proximally so that it can be pulled upon for operation. For example, the delivery device 1 may include a proximal handle (not shown) with a user operable mechanism for gripping and pulling the pull member 10. The distal tip member 5 includes a circumferential recess 11 and the fold portion 9 of the retaining sheath 4 is seated in this recess 11.

The retaining sheath 4 is made of cold drawn PET in the present embodiment, which is in accordance with the first aspect of the present invention. The stent device 3 is a self expanding stent device made of Nitinol. The pull member 10 is made of metal and is radially thicker than the outer sheath 8.

In use, the delivery device 1 is fed to a treatment site within the vasculature of the human body. The delivery device 1 is in the delivery configuration as it passes to the treatment site. A guide wire may be used, which extends through the inner member 2, so that the inner member 2 passes over the guide wire to guide the delivery device 1 to the treatment site. When the stent device 3 is located as desired, a pull end of the pull member 10 is pulled upon. This moves the pull member 10 proximally to slide the coupling ring 12 proximally. The outer sheath 8 of the retaining sheath 4 moves proximally with the coupling ring 12, which causes the outer sheath to slide over the inner sheath 7, which results in the fold portion 9 of the retaining sheath 4 to move or roll proximally. After a certain amount of proximal rolling, the fold portion 9 will move axially out of the recess 11 in the distal tip member 5 and begin to retract proximally over the stent device 3. As the fold portion 9 moves proximally in this way, the stent device 3 is uncovered, and thus released, from the retaining sheath 4. The stent device 3 expands to its deployment configuration along where the retaining sheath 4 has been retracted. Once the fold portion 9 moves beyond a proximal end of the stent device 3, the stent device 3 will be in its fully deployed configuration and thus supporting an inner wall of a diseased vein or artery. The coupling ring 12 and the retaining sheath 4 can continue to be pulled axially into the introducer member 6 by proximal movement of the pull member 10 until the retaining sheath becomes taught because the fold portion 9 is prevented from further proximal movement by the attachment of the retaining sheath 4 to the inner member 2. With the stent device 3 expanded to the deployed configuration, the distal tip member 5 can move proximally through a central lumen of the stent device 3 and be withdrawn from the body.

Figure 2:
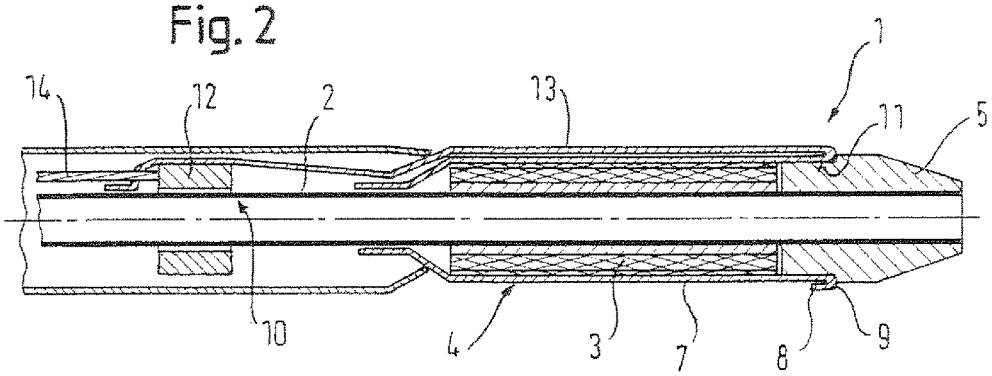
FIG. 2 discloses a second embodiment of a delivery device of the present invention having a retaining sheath that is retractable by rolling, wherein the retaining sheath is single walled along a full length of a stent device and a pull line is integrally formed with the retaining sheath and extends from a distal end of the stent device to proximally of the stent device.

A second embodiment of a delivery device, which is in accordance with the first and second aspects of the present invention, will be described with respect to FIG. 2. In the following discussion, differences with the delivery device of FIG. 1 will be concentrated upon. Like elements of the first and second embodiments share the same reference numerals.

An inner sheath 7 of the retaining sheath 4 is again attached to the inner member 2 at a location proximal of the stent device 3. The inner sheath 7 extends radially over and axially along the stent device 2 to a point distally beyond the stent device 2 whereat the retaining sheath 4 is folded back to provide an outer sheath 8 and a folded portion 9 between the inner sheath 7 and the outer sheath 8. The outer sheath 8 extends only a small distance proximally from the fold portion 9, but not far enough to be positioned radially over the stent device 3. The fold portion 9 and the full extent of the outer sheath 8 are positioned axially within the recess 11 of the distal tip member 5. It is noteworthy here that the sheath 4 is considered to end where it no longer defines a full circumferential cross-section and thus loses its sheath character. Proximally beyond the end of the outer sheath 8, an extension of the retaining sheath material is formed into a thread by weaving a number of strips of retaining sheath material into the thread. In this way, a pull line 13 is provided that is integral with the retaining sheath 4. The pull line 13 extends proximally along the stent device 3 and radially over the inner sheath 7. The pull member 10 comprises the pull line 13, the coupling ring 12 and a proximal pull wire 14. At a proximal end of the pull line 13, the pull line 13 is fixed to the coupling ring 12. The coupling ring 12 is also fixed to the pull wire 14, which extends proximally, perhaps to a proximal handle of the delivery device 1, to provide a pull end for an operative to pull upon.

In order to retract the retaining sheath 4, the pull wire 14 of the pull member 10 is moved proximally. This causes the coupling ring 12 and thus the pull line 13 to move proximally. The pull line 13 thus moves the outer sheath 8 proximally over the inner sheath 7, thereby rolling the fold portion 9 proximally. This functions despite the pull line 13 having only a minor circumferential extent as compared to the tubular outer sheath 8. It is believed that the use of a cold drawn plastic retaining sheath 4, and the ease with which it rolls, contributes to allowing a much thinner pull line 13, in the circumferential direction, to be effective in rolling back a circumferential retaining sheath 4. It may have been thought that where the pulling force on the outer sheath 8 is concentrated at a limited circumferential point by a pull line 13, then the retaining sheath 4 may not roll effectively and may instead drag at a location diametrically opposite to the pull line 13. This has been found not, necessarily, to be the case. The pull member 10 continues to be moved proximally to affect retraction of the retaining sheath 4 by rolling proximally, as has been described already, until the retaining sheath 4 is fully retracted and the stent device 3 is fully deployed.

Figure 3:
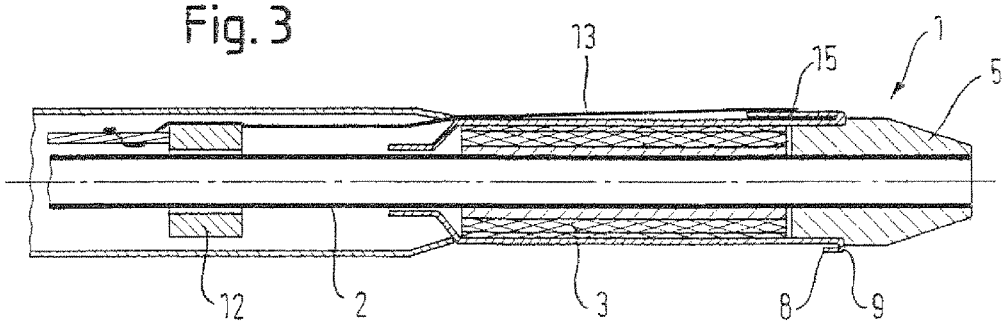
FIG. 3 discloses a third embodiment of a delivery device of the present invention having a retaining sheath that is retractable by rolling, wherein the retaining sheath is single walled along a full length of the stent device and a pull line made of a plastic thread extends from a distal end of the stent device to proximally of the stent device.

A third embodiment of both the first and second aspects of the present invention is shown in FIG. 3. It is the differences with the delivery device of figure that will be discuss in the following. The reference numerals are the same as with the delivery device of FIG. 2.

Instead of an integral pull line 13 as in the delivery device of FIG. 1, the pull line is provided, in the preferred embodiment, as a plastic, preferably nylon, thread. The inner sheath 7 is, as before, attached to the inner member 2 at a position proximal of the stent device. The inner sheath 7 extends radially over the stent device 3 and distally therealong to a point distal of the stent device 3 where the retaining sheath 4 is folded back upon itself to provide a fold portion 9 and an outer sheath 8. The outer sheath 8 and the fold portion 9 reside axially within the circumferential recess 11 in the distal tip member 5. A strip of the retaining sheath material extends proximally from the proximal end of the outer sheath 8 to a point just proximal of a distal end of the stent device 3, thereby providing an extension portion 15 of retaining sheath material. The extension portion 15 is provided so that the nylon thread pull line 13 can be securely attached thereto and thus fixed relative to the retaining sheath 4. They could be attached together by stitching or by adhesive for example. The pull line 13 extends radially over and proximally along the stent device 3 to axially within the introducer member 6 where it is fixed to the coupling ring 12.

To retract the retaining sheath 13, the pull member 10 is moved proximally by action on the pull wire 14. The proximal movement is transferred to the pull line 13 via the proximally sliding coupling ring 12. The pull line 13 pulls back on the retaining sheath material extension portion 15 to roll the retaining sheath proximally. The proximal rolling of the outer sheath 8 over the inner sheath 7 causes the fold portion 9 to move progressively proximally past the recess 11 and past the stent device 3 until it is fully retracted and contained axially within the introducer member 6. The stent device 3 radially expands into a deployed configuration as the retaining sheath 4 is retracted until it is fully deployed when the retaining sheath 4 is axially past the stent device 3. The pull line 13 and the extension portion 15 have a significantly reduced circumferential extent as compared to the closed circumference of the retaining sheath 4. Nonetheless, it has been found that retaining sheath 4 constructed according to the present invention rolls effectively during retraction without dragging or sticking.

In the above discussion, reference has been made to cold-drawn polymers as sheath material. The following disclosure gives one example as to how a stent may be loaded into a delivery sheath, which is subsequently cold-drawn.

Figure 4:
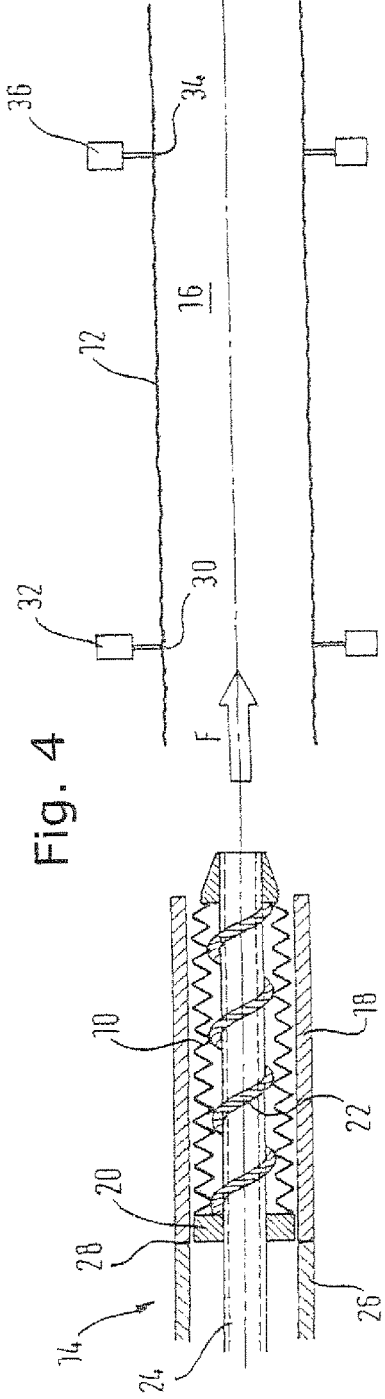
FIG. 4 discloses a longitudinal axial section through a device for loading a stent into a delivery sheath.

Reference numerals in the below disclosure relate to FIGS. 4, 5 and 6 only. FIG. 4 shows a crimped covered stent 10 ready for deploying from a loading sheath into a delivery sheath 12, by advancing the stent 10, in a loading tool 14 into the lumen 16 of the sheath 12, in the direction of arrow F.

The loading sheath is similar to a conventional stent deployment sheath, sized to be at least the length of the stent together with a further approximate 20% in length to provide a tolerant landing zone for the stent. It is conventionally of a braided polymer catheter material, as is generally known in the art of stent delivery systems.

The stent 10 is a radially self-expanding nickel titanium alloy stent covered in an ePTFE film. This covered stent is constrained by a loading sheath 18 in a radially compact disposition. The stent is installed in the loading sheath 18 by a "crimping" procedure known per se in which a jig (not shown) compresses the stent radially inwardly, down to its compact disposition, whereupon the stent 10 and the loading sheath 18 are moved relative to each other axially (usually by holding the sheath 18 stationary and translating the stent 10 into the lumen of the sheath 18).

In the present example, before the stent is crimped, there is inserted in its lumen a shaft 24 carrying a sequence of rings standing proud of the cylindrical surface of the shaft, or a spiral thread 22 running along the shaft. The covered stent is crimped down onto the shaft, whereupon the shaft can push the stent along its axis, supporting the stent all the way along the length of the stent, within its lumen.

The stent 10 is then "deployed" into the lumen 16 of the delivery sheath 12. For that deployment, the confining sheath 18 is pulled proximally by a pulling tube 26 contiguous with the proximal end 28 of the loading sheath 18.

During this pulling, one restrains the shaft 24 from axial movement, which prevents the stent from moving axially with the retreating loading sheath 18, so that the sheath remains in the desired location, inside the delivery sheath 12.

The delivery sheath 12 is of rather thin-walled PET tubular material. It is gripped at its proximal end 30 by an annular gripper chuck 32 and gripped at its distal end 34 by a similar annular gripping chuck 36, so that the two chucks 32 and 36 hold the opposite ends 30 and 34 of the delivery sheath 12 at a desired distance apart, while the stent is deployed into the sheath lumen 16.

Figure 5:
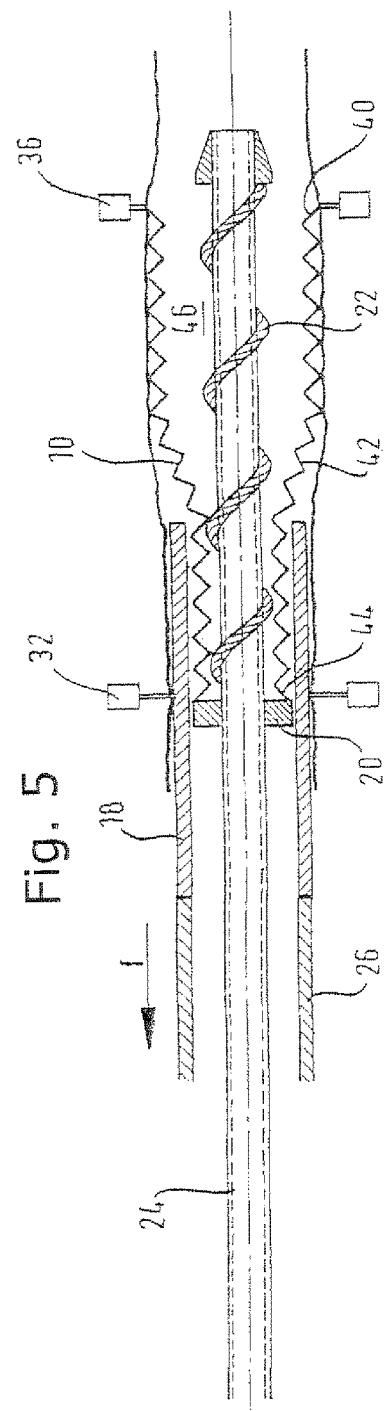
FIG. 5 disclose the device of FIG. 4, but with the stent partially loaded in the sheath.

This deployment process can be seen, partially completed, in FIG. 5 of the drawings, where like reference numerals identify the same components as are shown in FIG. 4. It will be appreciated that the loading sheath 18 has moved proximally, in the direction of arrow f, relative to the stent and to the stent pusher annulus 22, thereby releasing the stent 10 into the lumen 16 of the delivery sheath 12 progressively, starting at the distal end 40 of the stent, through a radially expanding portion 42 of the stent that travels the full length of the stent, from the distal end 40 to the proximal end 44 of the stent, not yet free of the confining loading sheath 18 as shown in FIG. 2. Once the full length of the stent 10 is clear of the loading sheath 18, the full radially outwardly directed stenting force from the stent 10 is carried by the delivery sheath 12, and the lumen 46 of the stent is big enough for simple proximal withdrawal from that lumen of the tubular element 24 of the loading machine.

As explained above, the stent 10 is now radially confined within the delivery sheath 12 and can be regarded as a precursor for a "capsule" for placement at the distal end of a catheter delivery system for the stent. If desired, the loading sheath can be reused a number of times, for example ten times, before it is replaced.

The process is presented in a block diagram, in drawing FIG. 6. However, FIG. 6 identifies further steps of the manufacturing process. The sequence of steps in FIG. 6 is identified by references A to I and we have the following comments on these process steps.

Step A is the step of providing the stent or stent graft of choice. A bare stent is one without any covering. A stent graft is a covered bare stent and the covering is typically of expanded polytetrafluoroethylene (ePTFE) but other covering materials are known to those skilled in the art.

Step B is the step of installing in the lumen of the chosen stent an inner catheter tool and the one preferred by the present Applicant is that described in its earlier publication WO 2004/096091 which goes by the acronym "ALFER," and which is incorporated by reference in its entirety into this application.

Step C is the step of crimping the stent to bring the outside diameter of the chosen stent down to one that is small enough for loading the crimped stent into the chosen loading sheath 18. Next, step D, the crimped stent is translated axially into the lumen of the loading sheath 18. Then, the loading sheath carrying the stent is translated (as explained in FIGS. 4 and 5) into the lumen 16 of the delivery sheath 12 and the loading sheath 18 is withdrawn in order to deploy the stent into the delivery sheath. As noted on FIG. 6, the delivery sheath 12 is conveniently a PET tube having a length about three times that of the stent, with a pre-thinned zone in the PET tube located midway along the length of the stent in the lumen of the PET tube.

Once the stent is deployed, the inner catheter loading tool can be removed, step F, from the lumen of the deployed stent. At this point, step G, any desired component of the catheter delivery system which is to be located in the lumen of the stent can now be introduced into that lumen.

Of course, other methods of deploying stents into the lumens of e.g. body passages are known by those skilled in the art, and may with appropriate modification be employed to deploy the stent from the loading sheath to the delivery sheath in an equivalent manner.

Having prepared the stent lumen, the delivery sheath can now be cold-drawn, lengthwise, to impose substantial strain on the material of the delivery sheath. This strain will have the effect of reducing the wall thickness of the delivery sheath, and generating hoop stresses within the delivery sheath being cold-drawn, which hoop stresses will tend to compress the stent inside the lumen of the delivery sheath, and therefore marginally reduce its diameter. The FIG. 6 block diagram carries notes in relation to this step H of the process. These notes teach to use a soft sticky material to grip the delivery sheath for achieving the cold-drawing strain. Such soft, sticky materials could be silicone rubber or an adhesive composition, for example. That strain is conveniently imposed on the sheath stepwise, commencing at the midpoint of the length of the sheath and repeating the cold-drawing process, stepwise, until a final desired outside diameter profile is achieved for the sheathed stent. For example, using two gripping chucks 32 and 36, the sheath is firstly gripped at each end by the two chucks. The chucks are drawn apart to create a weak zone at the middle of the sheath. Then, the sheath is simultaneously gripped in the middle by the first gripping chuck and at one end by the second gripping chuck, then the gripping chucks are slowly drawn apart. The second gripping chuck is now moved to the new middle of the drawn sheath, and the first gripping chuck to the other end. The gripping chucks are again drawn apart. This process is repeated until a desired delivery sheath diameter is reached.

Thus, in the final step I of the process, the stent-bearing capsule is ready for combining with other components of the catheter system that is to deliver the stent to the site of stenting in the body of a patient. This is done in an entirely conventional manner, for example heat-melting the inner catheter 24 with a member of the same diameter in the proximally proximate component of the delivery system.

In reading the present application, the skilled person may envisage a number of modifications without departing from the ambit of the claims.

For example, the preferred embodiments given above have the pull member being pulled to retract the retaining sheath. One can imagine that the pull member could be held steady while the inner catheter is moved distally, which would also have the effect of exposing the stent device from the retaining sheath. It is relative movement between the pull member and the stent device that is effective.

It is also possible that in the second and third embodiments the pull line could extend all the way proximally to a proximal end of the delivery device to be acted upon by an operative. In such a modified delivery device, the coupling ring and the pull wire could be done away with.

In the second and third embodiments, the retaining sheath is folded back on itself in the pre-retraction configuration (before the pull member has been moved proximally to any extent). One can envisage, however, the retaining sheath being flat or unfolded in the pre-retraction configuration and the pull line joining with a distal end wall of the retaining sheath. In such a modified embodiment, it is only once the pull line is pulled back that the retaining sheath folds back onto itself to provide the inner sheath, the outer sheath and the fold portion therebetween.

Accordingly, the invention is defined by the claims and the above presently preferred embodiment could be modified by the skilled person in a number of ways without departing from the invention.

What is claimed is:

1. A delivery device, comprising:
   an inner member coaxially disposed in an outer member;
   a stent device positioned over the inner member distal of the outer member, wherein the stent device is expandable from a radially reduced, delivery configuration to a radially expanded, deployed configuration;
   a tip member having a proximal end adjacent a distal end of the stent device, the proximal end of the tip member having a reduced diameter to form an annular recess;
   a retaining sheath disposed over the stent device for maintaining the stent device in the delivery configuration, the retaining sheath comprising a first material folded back on itself to provide:
   an inner portion;
   an outer portion; and a fold portion connecting the inner portion to the outer portion, the fold portion positioned in the annular recess in the delivery configuration; and a pull member coupled to the outer portion of the retaining sheath, the pull member comprising a pull wire disposed in the outer member, wherein proximal movement of the pull member moves the outer portion over the inner portion to move the fold portion proximally, thereby releasing the stent device for expansion to the deployed configuration, and wherein the outer portion of the retaining sheath terminates distal of a distal end of the stent device in the delivery configuration, further comprising an extension member coupled to the outer portion, wherein the extension member comprises a plurality of strips woven into a thread, each of the plurality of strips formed from the first material such that the extension member is integral with the retaining sheath.

2. The delivery device according to claim 1, further comprising: a coupler connected to the pull member, wherein the coupler is disposed outside of and coaxial with the inner member.

3. The delivery device of claim 1, wherein the inner portion of the retaining sheath is attached to the inner member at a position proximal of the stent device.

4. The delivery device of claim 1, wherein the retaining sheath moves into the outer member as the fold portion is moved proximally.

5. The delivery device of claim 4, further comprising a coupler connected to the pull member, the coupler positioned in the outer member in the delivery configuration.

6. The delivery device of claim 1, wherein the pull member is formed of a second material different from the first material.

7. The delivery device of claim 6, wherein the pull member has a thickness greater than a wall of the retaining sheath.

8. The delivery device of claim 1, wherein the first material is cold drawn polyester, and wherein the stent device comprises Nitinol.

9. The delivery device of claim 1, wherein the retaining sheath is a tube axially elongated in a range of 100% and 500% from a first length to a second length at a temperature below a glass transition temperature of the first material.

10. The delivery device of claim 9, wherein the first material is polyethylene terephthalate (PET).

* * * * *